United States Patent
Kovacs et al.

(10) Patent No.: US 6,953,673 B2
(45) Date of Patent: Oct. 11, 2005

(54) HISTAMINE H2 RECEPTOR AND USES

(75) Inventors: Karl F. Kovacs, Rockville, MD (US); Gilbert Jay, North Bethesda, MD (US)

(73) Assignee: Origene Technologies, Inc., Rockville, MD (US)

( * ) Notice: Subject to any disclaimer, the term of this patent is extended or adjusted under 35 U.S.C. 154(b) by 370 days.

(21) Appl. No.: 10/017,393

(22) Filed: Dec. 18, 2001

(65) Prior Publication Data

US 2003/0113839 A1 Jun. 19, 2003

(51) Int. Cl.[7] ............... C12N 15/12; C12N 15/63; C12N 15/00; C07H 21/04; C07K 14/00

(52) U.S. Cl. ................ 435/69.1; 435/320.1; 435/325; 435/6; 530/350; 536/23.1

(58) Field of Search .............. 435/6, 69.1, 320.1, 435/325; 530/350; 536/23.1

(56) References Cited

U.S. PATENT DOCUMENTS 5,994,506 A * 11/1999 Soppet et al. ............... 530/350

OTHER PUBLICATIONS

Voet et al. Biochemistry. 1990. John Wiley & Sons, Inc. pp. 126–128 and 228–234.*
Mickle JE et al. Genotype–phenotype relationships in cystic fibrosis. Med Clin North Am. 2000 May;84(3):597–607.*
Eck & Wilson in Goodman & Gilman's The Pharmacological Basis of Therapeutics. Ninth Edition. McGraw–Hill, New York, 1996, pp. 77–101.*

* cited by examiner

*Primary Examiner*—Joseph Murphy
(74) *Attorney, Agent, or Firm*—Millen, White, Zelano & Branigan, P.C.

(57) ABSTRACT

The present invention relates to the histamine H2 receptor (H2R), a member of the G-protein-coupled heptahelical receptor family. This novel H2 receptor codes for a novel carboxy-terminal tail which imparts important regulatory functions to the receptor, e.g., in down-regulation, signal transduction, and in coupling the activity of the H2R to downstream effector molecules, such as G-protein-coupled receptor kinases (GRK). The present invention relates to all facets of this new form of the H2R receptor, including nucleic acids that encode it, H2R polypeptides, binding-partners thereto, as well as its use in research, diagnosis, drug discovery, validation, and targeting, therapy, and clinical medicine.

14 Claims, No Drawings

SEQUENCE LISTING

```
<160> NUMBER OF SEQ ID NOS: 2

<210> SEQ ID NO 1
<211> LENGTH: 4175
<212> TYPE: DNA
<213> ORGANISM: Homo sapiens
<220> FEATURE:
<221> NAME/KEY: CDS
<222> LOCATION: (103)..(1371)
<223> OTHER INFORMATION:

<400> SEQUENCE: 1
gttgggagct tggagtccag tggttggcat agttgtcaca ttgggagcag agaagaagca      60
accaggggcc ctgatcaggg gactgagccg tagagtccca gg atg gca ccc aat      114
                                               Met Ala Pro Asn
                                                 1 ggc aca gcc tct tcc ttt tgc ctg gac tct acc gca tgc aag atc acc      162
Gly Thr Ala Ser Ser Phe Cys Leu Asp Ser Thr Ala Cys Lys Ile Thr
 5                  10                  15                  20 atc acc gtg gtc ctt gcg gtc ctc atc ctc atc acc gtt gct ggc aat      210
Ile Thr Val Val Leu Ala Val Leu Ile Leu Ile Thr Val Ala Gly Asn
                 25                  30                  35 gtg gtc gtc tgt ctg gcc gtg ggc ttg aac cgc cgg ctc cgc aac ctg      258
Val Val Val Cys Leu Ala Val Gly Leu Asn Arg Arg Leu Arg Asn Leu
             40                  45                  50 acc aat tgt ttc atc gtg tcc ttg gct atc act gac ctg ctc ctc ggc      306
Thr Asn Cys Phe Ile Val Ser Leu Ala Ile Thr Asp Leu Leu Leu Gly
         55                  60                  65 ctc ctg gtg ctg ccc ttc tct gcc atc tac cag ctg tcc tgc aag tgg      354
Leu Leu Val Leu Pro Phe Ser Ala Ile Tyr Gln Leu Ser Cys Lys Trp
     70                  75                  80 agc ttt ggc aag gtc ttc tgc aat atc tac acc agc ctg gat gtg atg      402
Ser Phe Gly Lys Val Phe Cys Asn Ile Tyr Thr Ser Leu Asp Val Met
 85                  90                  95                 100
```

-continued

| | |
|---|---|
| ctc tgc aca gcc tcc att ctt aac ctc ttc atg atc agc ctc gac cgg<br>Leu Cys Thr Ala Ser Ile Leu Asn Leu Phe Met Ile Ser Leu Asp Arg<br>105                110                115 | 450 |
| tac tgc gct gtc atg gac cca ctg cgg tac cct gtg ctg gtc acc cca<br>Tyr Cys Ala Val Met Asp Pro Leu Arg Tyr Pro Val Leu Val Thr Pro<br>    120                125                130 | 498 |
| gtt cgg gtc gcc atc tct ctg gtc tta att tgg gtc atc tcc att acc<br>Val Arg Val Ala Ile Ser Leu Val Leu Ile Trp Val Ile Ser Ile Thr<br>135                140                145 | 546 |
| ctg tcc ttt ctg tct atc cac ctg ggg tgg aac agc agg aac gag acc<br>Leu Ser Phe Leu Ser Ile His Leu Gly Trp Asn Ser Arg Asn Glu Thr<br>    150                155                160 | 594 |
| agc aag ggc aat cat acc acc tct aag tgc aaa gtc cag gtc aat gaa<br>Ser Lys Gly Asn His Thr Thr Ser Lys Cys Lys Val Gln Val Asn Glu<br>165                170                175                180 | 642 |
| gtg tac ggg ctg gtg gat ggg ctg gtc acc ttc tac ctc ccg cta ctg<br>Val Tyr Gly Leu Val Asp Gly Leu Val Thr Phe Tyr Leu Pro Leu Leu<br>    185                190                195 | 690 |
| atc atg tgc atc acc tac tac cgc atc ttc aag gtc gcc cgg gat cag<br>Ile Met Cys Ile Thr Tyr Tyr Arg Ile Phe Lys Val Ala Arg Asp Gln<br>200                205                210 | 738 |
| gcc aag agg atc aat cac att agc tcc tgg aag gca gcc acc atc agg<br>Ala Lys Arg Ile Asn His Ile Ser Ser Trp Lys Ala Ala Thr Ile Arg<br>    215                220                225 | 786 |
| gag cac aaa gcc aca gtg aca ctg gcc gcc gtc atg ggg gcc ttc atc<br>Glu His Lys Ala Thr Val Thr Leu Ala Ala Val Met Gly Ala Phe Ile<br>230                235                240 | 834 |
| atc tgc tgg ttt ccc tac ttc acc gcg ttt gtg tac cgt ggg ctg aga<br>Ile Cys Trp Phe Pro Tyr Phe Thr Ala Phe Val Tyr Arg Gly Leu Arg<br>245                250                255                260 | 882 |
| ggg gat gat gcc atc aat gag gtg tta gaa gcc atc gtt ctg tgg ctg<br>Gly Asp Asp Ala Ile Asn Glu Val Leu Glu Ala Ile Val Leu Trp Leu<br>    265                270                275 | 930 |
| ggc tat gcc aac tca gcc ctg aac ccc atc ctg tat gct gcg ctg aac<br>Gly Tyr Ala Asn Ser Ala Leu Asn Pro Ile Leu Tyr Ala Ala Leu Asn<br>280                285                290 | 978 |
| aga gac ttc cgc acc ggg tac caa cag ctc ttc tgc tgc agg ctg gcc<br>Arg Asp Phe Arg Thr Gly Tyr Gln Gln Leu Phe Cys Cys Arg Leu Ala<br>    295                300                305 | 1026 |
| aac cgc aac tcc cac aaa act tct ctg agg tcc aac gcc tct cag ctg<br>Asn Arg Asn Ser His Lys Thr Ser Leu Arg Ser Asn Ala Ser Gln Leu<br>310                315                320 | 1074 |
| tcc agg acc caa agc cga gaa ccc agg caa cag gaa gag aaa ccc ctg<br>Ser Arg Thr Gln Ser Arg Glu Pro Arg Gln Gln Glu Glu Lys Pro Leu<br>325                330                335                340 | 1122 |
| aag ctc cag gtg tgg agt ggg aca gaa gtc acg gcc ccc cag gga gcc<br>Lys Leu Gln Val Trp Ser Gly Thr Glu Val Thr Ala Pro Gln Gly Ala<br>    345                350                355 | 1170 |
| aca gac agg aag cca gca ctg tcc tgc act acg tgc tcc agc aac ctc<br>Thr Asp Arg Lys Pro Ala Leu Ser Cys Thr Thr Cys Ser Ser Asn Leu<br>360                365                370 | 1218 |
| ctg agc tgc tgc aag agc ctg tgg ggg ctc agg ttc ctt cag aga cac<br>Leu Ser Cys Cys Lys Ser Leu Trp Gly Leu Arg Phe Leu Gln Arg His<br>    375                380                385 | 1266 |
| atg gga ggc ccc tcg gag gag cta tcg ggg gag cca ctg tct gag gag<br>Met Gly Gly Pro Ser Glu Glu Leu Ser Gly Glu Pro Leu Ser Glu Glu<br>390                395                400 | 1314 |
| cca cag aag aga cct ccc cag aaa gcg gtg agg acg ctg ccc tct gag<br>Pro Gln Lys Arg Pro Pro Gln Lys Ala Val Arg Thr Leu Pro Ser Glu | 1362 |

-continued

```
                405         410         415         420
gct gtc tag acctagcccc aggacactga agataccgct cccgtcccc        1411
Ala Val
aagatgtgac tcctggagct cctaaggacc cagtctccaa agccaccaag gactcaccct 1471
ggactgaatc tgggggctcc cagaacacac agctgggtgt ggggtcctca ggcctagggc 1531
ggaacagcct attctgtgct cagcattccc agacaggcac gcaagactcc tctgggcccg 1591
agtgggctga atcccatggg ttcaaagctc acgttggtgc tggccctggg agtcatgagc 1651
agagacggtg ggacagacgg ggatgcgtgc acatgtgtgt gcatgggtgc atacgtgtag 1711
ggacgtgcat gacctctgag caaggcagag ggtattgaag aaagcattgg cctctcactc 1771
cctcatgggt tctgcaggat gaaggaaagg aaaggaaaag acagagaaag gaaggaaata 1831
gcttttcatg agcacctact gtgtaccagg tgcttccctg gcatgagctc tcgtaacct  1891
tatagcaaca tgagtttaga gcaagaatca caccccgact ttacagagat ggaaactgag 1951
gctcagagaa gtaagggacc tgcccaaggc cactcagcac ctagaaagtg tgcctagcac 2011
ataggaggca cacaaaaata tgtgttgaat gggtgaatga atgagagaac gggtgaaaag 2071
ccaggcctca agcccacact actgacactg cactacacca cctctcagga gagaaggcaa 2131
atatttcctt gactcagcca ccttcctcct agcaaggctt agaccccag gctctggggg 2191
tcccttcctg ctacagtatg accctctctg gtgcttgtca tcaagaagtg gtatgcggtg 2251
gacttgctgg agagagtgtc tgcagccagg catcatggag ggagggatgg atcttgaggg 2311
actgtaatgg ttgtgaatgg gggagttggc ccccagcact ctctggtggc cgtatgacct 2371
tgggcacgtc tcctgaccac tctaagcagc ttttgattcc cctgtccaag agggtaggcc 2431
ccctgttcct atttacagga tccataaaga gactcaaaga gatagggtag tgccagcccc 2491
agagagaggg ggctgtggag ggacttctac ccccagggct tctcagtggc atctcctggc 2551
tggcccctga cactcaatct tccttggttt ccaagatgct tcatgatctt cccctccct  2611
gacatccccg acctccctt tctgtccctt ttgcaactca ttgtcctcta cctgccatca  2671
gatgtggctg ttcctcagtc tcagtccaga gtcctctctt ctcactcagc atctctcctc 2731
ctgtgacctc gtctgcaccc acaactccag ttacaaggca cgaggtttgg ttatgaaatc 2791
actcacagat ttataactgc aggcttggct ccttccggga gcttgagacc cactgccgcc 2851
tccgcaacac ctccacctgg gagtttcaga ggcgctctcc ctcagcgtgt ctgcagctgc 2911
gtgcctgcag ctgcgtgcct gccttctccc tgcacctgct ctgctcccca ggtccctttc 2971
tcagaccaaa gcctgcccgg gcttcacagg ctgagggtcc accttgccac ctccgtttgc 3031
ctcagtcctc atggagccct ggctccactg tctgctggct tctccccatc tactctgtgt 3091
cactccatcc gaccaccatt gtctccatca ggacagttgg aacacctctt ctcagcactc 3151
tcgcccccac ccagtccacc ccctacctga cagccagagt gggccatgcc agatgcaacc 3211
caggtcatgc cacacaggta gataaaacca tcttcagccc agccctcagg ccctgtgtgc 3271
tgggaccctg ctgggccctc tccagcctcc cctgcgcca ggcctcctcc gtcacttcac  3331
tctggccctg ctgttctttt ccttttagtt tgattaactc actctgccca ttccatgctc 3391
aaagctgttt ccgtgaggaa aggctcctcc tgctcatttt agtgccctga aatgtcactt 3451
ccttgaggaa gtcttccttg accctccaca ccaaaccagg cccctgcca caccctcag  3511
agctctcctt ggaaggcact ggcatggctg tttgcgtgat tccttgaacg ttgtctgtct 3571
ctcctcctca ccaggctgtg ggtcctgtct gtttctggtg accgttgtct gtctaacccc 3631
```

-continued

```
tagaggagag tttgtcacat ggtaggagct taataaatat gtgttggatg aatgatcaga    3691 gaaagagag tgcagagagt ggccaaaaca gatgctttca gcagtgtatc tgccaataaa    3751
cctaaaggca tgatttgccc tggtgatccc cccagaggtg cttagtctct tggctgaatt    3811
ccttctggaa tccccagaat cccctcctt ggaagttttc ccaggagtct gaggcaggca    3871
ggtctctcag tcacggccac atgacctcaa gtgaaaacaa accagtctgg ctgttcacag    3931
actcagctgg tcagagctct ggcccgaggg gcccacgcac cacccgccac tgcagaagac    3991
gcctccacgt ctgtctctgg gctgcctcca ccttctgcag gcctcctgga gcctctgctg    4051
gctgcagaag tggggtgcat gctgcctgga ggaggaacat ctgtggtggg accccaaatc    4111
catgtttgtg ttaccatcgt gttccaataa aactatcgaa acagaaaaaa aaaaaaaaa    4171 aaaa                                                                  4175
```

<210> SEQ ID NO 2
<211> LENGTH: 422
<212> TYPE: PRT
<213> ORGANISM: Homo sapiens

<400> SEQUENCE: 2

```
Met Ala Pro Asn Gly Thr Ala Ser Ser Phe Cys Leu Asp Ser Thr Ala
 1               5                  10                  15

Cys Lys Ile Thr Ile Thr Val Val Leu Ala Val Leu Ile Leu Ile Thr
            20                  25                  30

Val Ala Gly Asn Val Val Val Cys Leu Ala Val Gly Leu Asn Arg Arg
        35                  40                  45

Leu Arg Asn Leu Thr Asn Cys Phe Ile Val Ser Leu Ala Ile Thr Asp
    50                  55                  60

Leu Leu Leu Gly Leu Leu Val Leu Pro Phe Ser Ala Ile Tyr Gln Leu
65                  70                  75                  80

Ser Cys Lys Trp Ser Phe Gly Lys Val Phe Cys Asn Ile Tyr Thr Ser
                85                  90                  95

Leu Asp Val Met Leu Cys Thr Ala Ser Ile Leu Asn Leu Phe Met Ile
            100                 105                 110

Ser Leu Asp Arg Tyr Cys Ala Val Met Asp Pro Leu Arg Tyr Pro Val
        115                 120                 125

Leu Val Thr Pro Val Arg Val Ala Ile Ser Leu Val Leu Ile Trp Val
    130                 135                 140

Ile Ser Ile Thr Leu Ser Phe Leu Ser Ile His Leu Gly Trp Asn Ser
145                 150                 155                 160

Arg Asn Glu Thr Ser Lys Gly Asn His Thr Thr Ser Lys Cys Lys Val
                165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Tyr Arg Ile Phe Lys Val
        195                 200                 205

Ala Arg Asp Gln Ala Lys Arg Ile Asn His Ile Ser Ser Trp Lys Ala
    210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Ala Phe Val Tyr
                245                 250                 255

Arg Gly Leu Arg Gly Asp Asp Ala Ile Asn Glu Val Leu Glu Ala Ile
            260                 265                 270
```

-continued

```
Val Leu Trp Leu Gly Tyr Ala Asn Ser Ala Leu Asn Pro Ile Leu Tyr
        275                 280                 285

Ala Ala Leu Asn Arg Asp Phe Arg Thr Gly Tyr Gln Gln Leu Phe Cys
    290                 295                 300

Cys Arg Leu Ala Asn Arg Asn Ser His Lys Thr Ser Leu Arg Ser Asn
305                 310                 315                 320

Ala Ser Gln Leu Ser Arg Thr Gln Ser Arg Glu Pro Arg Gln Gln Glu
                325                 330                 335

Glu Lys Pro Leu Lys Leu Gln Val Trp Ser Gly Thr Glu Val Thr Ala
            340                 345                 350

Pro Gln Gly Ala Thr Asp Arg Lys Pro Ala Leu Ser Cys Thr Thr Cys
        355                 360                 365

Ser Ser Asn Leu Leu Ser Cys Cys Lys Ser Leu Trp Gly Leu Arg Phe
    370                 375                 380

Leu Gln Arg His Met Gly Gly Pro Ser Glu Glu Leu Ser Gly Glu Pro
385                 390                 395                 400

Leu Ser Glu Glu Pro Gln Lys Arg Pro Pro Gln Lys Ala Val Arg Thr
                405                 410                 415

Leu Pro Ser Glu Ala Val
                420
```

HISTAMINE H2 RECEPTOR AND USES

DESCRIPTION OF THE DRAWINGS

SEQ ID NO 1 shows the nucleotide sequence of a human H2R and SEQ ID NO 2 shows the amino acid sequence of a human H2R.

DESCRIPTION OF THE INVENTION

The present invention relates to the histamine H2 receptor (H2R), a member of the G-protein-coupled heptahelical receptor family. A genomic DNA coding for a H2R was originally identified in 1991 from a dog genomic library. Receptor homologs were subsequently isolated from a number of mammalian species. It has now been found that the H2R receptors as previously identified were incomplete, lacking a substantial portion of the C-terminus that projects into the cell cytoplasm. Despite years of intensive research on this medically important receptor, this deficiency went unnoticed. Strikingly, the human form of this novel H2 receptor codes for a 422 amino acid polypeptide, 63 more amino acids than present in the previously known form. Compare, e.g., U.S. Pat. No. 5,885,824. These additional carboxy-terminal residues encode important regulatory functions, e.g., in down-regulation, signal transduction, and in coupling the activity of the H2R to downstream effector molecules, such as G-protein-coupled receptor kinases (GRK). The present invention relates to all facets of this new form of the H2R receptor, including nucleic acids that encode it, H2R polypeptides, binding-partners thereto, as well as its use in research, diagnosis, drug discovery, validation and targeting, therapy, and clinical medicine.

Histamine H2 Receptor

Histamine is a biogenic amine involved in a number of physiological processes, including, vascular dilation, smooth muscle contraction, inflammation, and gastric acid secretion. It is also a neurotransmitter in the brain.

Histamine's activity is mediated by several different subtypes of the histamine receptors. The histamine receptor 1 (H1R) is involved in vascular dilation and smooth muscle contraction. Receptor subtype 2 (H2R) is found at high levels in the stomach, but in lower numbers in the heart, brain, smooth muscle, and cells of the immune system. In the stomach, it is present in gastric parietal cells where stimulation of it leads to gastric acid secretion. The discovery of selective antagonists for the H2 receptor revolutionized the treatment of gastric ulcers, providing specific drugs which could target the gastric mucosa, without affecting other histaminergic processes. For a review, see, e.g., Del Valle and Gantz, *Am. J. Physiol.*, 236:G987–G996, 1997. In addition to its well known role in gastric acid secretion, the H2 receptor is also involved in other processes, including, e.g., gastrointestinal motility, intestinal secretion, cell growth, and differentiation.

The gene coding for the H2 receptor was cloned in 1991 from canine genomic DNA. See, Gantz et al., *Biochem. Biophys. Res. Commun.*, 178:1386–1392, 1991; U.S. Pat. No. 5,885,824. Using oligonucleotide probes based on known GPCR receptors, Gantz et al. identified a partial clone from mRNA isolated from canine gastric parietal cells. This DNA was used as probe on a canine genomic library, resulting in the isolation of what was believed to be the full-length histamine H2 receptor. The gene was determined to be intronless, consistent with findings from other heptahelical G-protein coupled receptors. Since that initial report, genomic sequences of the H2 receptor were isolated from several different mammalian species, including, human, rat, and guinea pig. Ruat et al., *Biochem. Biophys. Res. Commun.*, 179:1470–1478, 1991; Traiffort et al., *Biochem. Biophys. Res. Commun.*, 211:570–577, 1995. All sequences agreed with the original conclusion that a full-length clone existed, and there was no doubt that these clones encoded the full-length H2R.

It was discovered herein that the published histamine type 2 receptor polypeptides and corresponding nucleic acids (e.g., XM_018146, NM_022304, NM_012965, and AB041386) were, in fact, incomplete, and that Gantz et al. and others had identified partial coding sequences (i.e., ESTs) for it. The present invention corrects this deficiency, describing a full-length H2R having a novel carboxy-terminal tail that possesses important regulatory functions. The complete nucleotide and amino acid of a human H2R is shown in SEQ ID NOS 1 and 2. H2Rs of the present invention contain two exons, while the H2R previously reported contain only a single exon. In the human, the second exon codes for amino acids 360–422 (SEQ ID NO 2) of the receptor protein, and had not been identified previously as part of the H2 receptor. The polypeptide for human H2R contains a signal peptide at about amino acids 1–26, and transmembrane domains at about amino acid positions 20–42, 55–77, 92–114, 135–157, 184–206, 232–254, and 269–291. In addition, it contains histamine receptor, type 2, motifs that distinguish it from the type 1 receptor. A canonical poly(A) signal AATAAA is found 19 base pairs upstream of poly(A) tail. All or part of the H2R is located in genomic DNA represented by GenBank ID: AC010219.4, BAC-ID: CTC-251I16, and Contig ID: NT_006928. Using UniSTS probes, the gene can be chromosomally mapped at its 5' end with UniSTS: 22639 to 179.4370 Mb, its 3' end with UniSTS: 29777 to 179.4635 Mb. It is located at chromosomal band 5q35. A "human H2R" means a polynucleotide or polypeptide having the full-length sequence as shown in SEQ ID NO 2, or polymorphisms of it which are naturally-occurring in humans.

Activation of the H2 receptor leads to the accumulation of cAMP in a number of systems, including the brain and stomach mucosal cells. This effect is believed to result from the direct stimulation of adenylate cyclase via a guanine-nucleotide dependent mechanism. The precise class of G-proteins involved in this pathway have not been identified. In addition to cAMP production, H2-receptor activation also leads other signal transduction events, including phospholipid methylation, changes in calcium conductance, mobilization of intracellular calcium pools, and inhibition of phospholipase A.

In gastric parietal cells, histamine can result in both an increase in cAMP and calcium. The calcium effect appears to be mediated by the phosphoinositide signaling pathway, whereas the cAMP effect is via adenylate cyclase stimulation. Experiments suggest that the effects are accomplished by the same receptor molecule, but through different signaling pathways. Evidence indicates that $G_S$-alpha is involved in coupling receptor stimulation to adenylate cyclase, but that another G-protein links it to the phosphoinositide signaling pathway.

The C-terminal intracellular tail of the H2 receptor has been shown to play a role in the internalization of the receptor in response to histamine stimulation. It also has an inhibitory effect on cAMP production. Fukushima et al., *J. Biol. Chem.*, 272:19464–19470, 1997. Studies using cell lines transfected with the receptor gene have shown it couples with GRK2 and GRK3, but not other GRKs or protein kinases A and C. Shayo et al., *Mol. Pharmacol.*, 60:1049–1056, 2001. All of these studies were performed with the H2R form which is now known to lack a substantial portion of the C-terminal tail.

The carboxy-terminus of the H2R as disclosed herein comprises various consensus sites for GRK-mediated phosphorylation. For instance, pairs of acidic residues are found at amino acid positions 394–395 and 403–404, a signature found at the amino-terminus of certain GRK phosphorylation sites. Fredericks et al., *J. Biol. Chem.*, 271:13796–13803, 1996. Phosphorylation of these sites is involved in uncoupling the receptor from adenylate cyclase, receptor desensitization, and other signaling activities mediated by the H2R.

As indicated above, the H2R is involved in a number of medically-important conditions, including, but not limited to, acid peptic disorders, gastric and duodenal ulcers, dyspepsia, gastro-esophageal reflux disease, and other disorders associated with aberrant histaminergic function (e.g., excess histamine, or insufficient histamine). H2Rs of the present invention can be used to screen and identify compounds which modulate such diseases (e.g., treat and/or prevent). In addition, they can be used to identify compounds, etc., which modulate any of the above-mentioned physiological processes associated with H2R function. In addition, receptors of the present invention can be used to develop and screen the selectivity of pharmacological agents for other histamine receptor types, including H1 and H3, as well as for ligands that show cross-specificity for more than one receptor type.

Nucleic Acids

A mammalian polynucleotide, or fragment thereof, of the present invention is a polynucleotide having a nucleotide sequence obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc.

Polynucleotides and polypeptides (including any part of H2R) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube. A polynucleotide which "codes without interruption" refers to a polynucleotide having a continuous open reading frame ("ORF") as compared to an ORF which is interrupted by introns or other noncoding sequences.

As explained in more detail below, a polynucleotide sequence of the invention can contain the complete sequence as shown in SEQ ID NOS 1 and 2, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NO 1 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NO 1 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NOS 1 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 μg/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 μg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M $NaPO_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 $\log_{10}[Na^+]$+0.41 (%GC)−600/N where [$Na^+$] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NOS 1 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, Drosophila, *C. elegans*, Xenopus, yeast such as *S. pombe*, *S. cerevisiae*, roundworms, prokaryotes, plants, Arabidopsis, artemia, viruses, etc. The degree of nucleotide sequence identity between human and mouse can be about, e.g. 70% or more, 85% or more for open reading frames, etc. Since the carboxy-terminal tail of the H2R has not been cloned from other species, the region from about amino acids 360–422 of SEQ ID NO 2 can be used to design probes and select homologs. The present invention relates to all probes within this region, as well as any methods of using them.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc.

Percent sequence identity can also be determined by other conventional methods, e.g., as described in Altschul et al., *Bull. Math. Bio.* 48: 603–616, 1986 and Henikoff and Henikoff, *Proc. Natl. Acad. Sci.* USA 89:10915–10919, 1992.

Specific Polynucleotide Probes

A polynucleotide of the present invention can comprise any continuous nucleotide sequence of nucleotides 1182–1368 of SEQ ID NO 1, or, coding for amino acids 360–422 of SEQ ID NO 2, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100, 8–75, 7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of nucleotides 1182–1368 (SEQ ID NO 1), or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for H2R, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample. It is specific in the sense that it can be used to detect polynucleotides above background noise ("non-specific binding"). A specific sequence is a defined order of nucleotides which occurs in the polynucleotide, e.g., in the nucleotide sequences of 1182–1368 (SEQ ID NO 1). A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human polynucleotide, in a sample comprising a mixture of polynucleotides, e.g., on a Northern blot, to detect homologs in other species (e.g., rat, mouse, dog, horse, gorilla, goat, sheep, cat, mammals, vertebrates, invertebrates, such as Drosophila, etc.). Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

Probes which are specific for polynucleotides of the present invention can also be prepared using involve transcription-based systems, e.g., incorporating an RNA polymerase promoter into a selective polynucleotide of the present invention, and then transcribing antisense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. Nos. 5,411,863; 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^{3}H$, or $^{14}C$, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting H2R. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., Science, 241:53, 1988; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99–115, 1997), ligase chain reaction ("LCR") (EP 320 308), one-sided PCR (Ohara et al., Proc. Natl. Acad. Sci., 86:5673–5677, 1989), indexing methods (e.g., U.S. Pat. No. 5,508,169), in situ hybridization, differential display (e.g., Liang et al., Nucl. Acid. Res., 21:3269–3275, 1993; U.S. Pat. Nos. 5,262,311, 5,599,672 and 5,965,409; WO97/18454; Prashar and Weissman, Proc. Natl. Acad. Sci., 93:659–663, and U.S. Pat. Nos. 6,010,850 and 5,712,126; Welsh et al., Nucleic Acid Res., 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., Proc. Natl. Acad, Sci., 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, Nature Biotech., 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., Methods Mol. & Cell. Biol. 2, 17–25, 1990; Eberwine et al., 1992, Proc. Natl. Acad. Sci., 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with H2R, for monitoring or assessing therapeutic and/or preventative measures, in ordered arrays, etc. Any method of detecting genes and polynucleotides of SEQ ID NOS 1 and 2 can be used; certainly, the present invention is not to be limited how such methods are implemented.

Along these lines, the present invention relates to methods of detecting H2R in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is a polynucleotide which is SEQ ID NO 1, a polynucleotide having, e.g., about 70%, 80%, 85%, 90%, 95%, 99%, or more sequence identity thereto, effective or specific fragments thereof, or complements thereto. Preferred probes are selected from 1182–1368 of SEQ ID NO 1. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NO 1 is desired, a probe can be selected which can hybridize to such target gene under high stringent conditions, without significant hybridization to other genes in the sample. To detect homologs of a polynucleotide set forth in SEQ ID NO 1, the effective hybridization conditions can be less stringent, and/or the probe can comprise codon degeneracy, such that a homolog is detected in the sample. Preferred polynucleotide probes are from the region of the carboxy-terminal tail, e.g., about from nucleotides 1182–1368 of SEQ ID NO 1.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of H2R

Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., Proc. Natl. Acad. Sci., 86:2766, 1992), etc., where a polynucleotide having a sequence selected from SEQ ID NOS 1 is used as a probe. Preferred probes are selected from positions 1182–1368 (i.e., amino acids 360–422) of SEQ ID NO 1. The selected mutant alleles, SNPs, polymorphisms, etc., can be used diagnostically to determine whether a subject has, or is susceptible to a disorder associated with H2R, as well as to design therapies and predict the outcome of the disorder. Methods involve, e.g., diagnosing a disorder associated with H2R or determining susceptibility to a disorder, comprising, detecting the presence of a mutation in a gene represented by a polynucleotide selected from SEQ ID NO 1. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al., Proc. Natl. Acad. Sci., 89:8779–8783, 1992.

The present invention also relates to methods of detecting polymorphisms in H2R, comprising, e.g., comparing the structure of: genomic DNA comprising all or part of H2R, mRNA comprising all or part of H2R, cDNA comprising all or part of H2R, or a polypeptide comprising all or part of H2R, with the structure of H2R set forth in SEQ ID NO 1 or 2, and genomic DNA thereof. The methods can be carried out on a sample from any source, e.g., cells, tissues, body fluids, blood, urine, stool, hair, egg, sperm, cerebral spinal fluid, etc.

These methods can be implemented in many different ways. For example, "comparing the structure" steps include, but are not limited to, comparing restriction maps, nucleotide sequences, amino acid sequences, RFLPs, Dnase sites, DNA methylation fingerprints (e.g., U.S. Pat. No. 6,214, 556), protein cleavage sites, molecular weights, electrophoretic mobilities, charges, ion mobility, etc., between a standard H2R and a test H2R. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093,541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., Ann. Rev. Genet. 19:423–463, 1985), degenerate oligonucleotide-directed (Hill et al., Method Enzymology, 155:558–568, 1987), region-specific (Myers et al., Science, 229:242–246, 1985; Derbyshire et al., Gene, 46:145, 1986; Ner et al., DNA, 7:127, 1988), linker-scanning (McKnight and Kingsbury, Science, 217:316–324, 1982), directed using PCR, recursive ensemble mutagenesis (Arkin and Yourvan, Proc. Natl. Acad. Sci., 89:7811–7815, 1992), random mutagenesis (e.g., U.S. Pat. Nos. 5,096,815; 5,198, 346; and 5,223,409), site-directed mutagenesis (e.g., Walder et al., Gene, 42:133, 1986; Bauer et al., Gene, 37:73, 1985; Craik, Bio Techniques, January 1985, 12–19; Smith et al., Genetic Engineering: Principles and Methods, Plenum Press, 1981), phage display (e.g., Lowman et al., Biochem. 30:10832–10837, 1991; Ladner et al., U.S. Pat. No. 5,223, 409; Huse, WIPO Publication WO 92/06204), etc. Desired sequences can also be produced by the assembly of target sequences using mutually priming oligonucleotides (Uhlmann, Gene, 71:29–40, 1988). For directed mutagenesis methods, analysis of the three-dimensional structure of the H2R polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In addition, libraries of H2R and fragments thereof can be used for screening and selection of H2R variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, xpression libraries can be made comprising "mutagenized" H2R. The entire coding sequence or parts thereof can be used.

Preferred mutations of H2R include mutations within the carboxy-tail, e.g., amino acids 360–422 of SEQ ID NO 2. For example serine and threonine resides within this region can be replaced with alanine, or other nonpolar amino acids, to study phosphorylation of the receptor protein. One or more serines or threonine can be changed at, e.g., positions 364, 366, 367, 369, 370, 374, 378, 393, 397, 402, 416, and/or 419. In addition, the acidic amino acid pairs at positions 394–395 and 403–404, can be replaced, e.g., with uncharged amino acids, etc.

Polynucleotide Expression, Polypeptides Produced Thereby, and Specific-binding Partners Thereto.

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, insect cells, such as Sf9 (*S. frugipeda*) and *Drosophila*, bacteria, such as *E. coli*, *Streptococcus*, bacillus, yeast, such as *Sacharomyces*, *S. cerevisiae*, fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.*, 12(18):7035–7056, 1984; Dunn and Studier. *J. Mol. Bio.*, 166:477–435, 1984; U.S. Pat. No. 5,891,636; Studier et al., *Gene Expression Technology, Methods in Enzymology*, 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NO 1, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862. A preferred polypeptide for expression comprises amino acids 360–422 (SEQ ID NO 2), including fragments of it.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6xHis, maltose binding protein, chitinase, etc) and then purify by anti-tag antibody-conjugated affinity chromatography.

The present invention also relates to antibodies, and other specific-binding partners, which are specific for polypeptides encoded by polynucleotides of the present invention, e.g., H2R. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.*, 86:3833–3837, 1989; Huse et al., *Science*, 256:1275–1281, 1989); in vitro stimulation of lymphocyte populations; Winter and Milstein, *Nature*, 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580,859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. Antibodies can be prepared against specific epitopes or domains of H2R, e.g., from about amino acids 360–422 of SEQ ID NO 2, or fragments thereof.

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat.

No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in E. coli of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V.sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., Science 242:423–426 (1988); Ladneret al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to H2R polypeptides of the present invention can be prepared using an intact polypeptide or fragments containing small peptides of interest as the immunizing antigen. For example, it may be desirable to produce antibodies that specifically bind to the N- or C-terminal domains of H2R. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by H2R of the present invention can be detected, visualized, determined, quantitated, etc. according to any effective method. useful methods include, e.g., but are not limited to, immunoassays, RIA (radioimmunassay), ELISA, (enzyme-linkedimmunosorbent assay), immunoflourescence, flow cytometry, histology, electron microscopy, light microscopy, in situ assays, immunoprecipitation, Western blot, etc. The preferred detection target is the carboxy-terminal tail, e.g., amino acids 360–422 of SEQ ID NO 2.

Immunoassays may be carried in liquid or on biological support. For instance, a sample (e.g., blood, stool, urine, cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled H2R specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads.

One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect H2R peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Diagnostic The present invention also relates to methods and compositions for diagnosing a H2R disorder or a histaminergic disorder associated with H2R (e.g., excess histamine secretion, such as occurs with peptic ulcers) or determining susceptibility to such disorders, using polynucleotides, polypeptides, and specific-binding partners of the present invention to detect, assess, determine, etc., H2R. In such methods, the gene can serve as a marker for the disorder, e.g., where the gene, when mutant, is a direct cause of the disorder; where the gene is affected by another gene or gene product which is directly responsible for the disorder, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a disorder related to H2R expression or function, or determining a subject's susceptibility to such disorder, comprising, e.g., assessing the expression of H2R in a tissue sample comprising tissue or cells suspected of having the disorder. The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. Diseases include, but are not limited to, acid peptic disorders, gastric and duodenal ulcers, dyspepsia, and gastro-esophageal reflux disease, diseases associated with H2R expression, e.g., in brain, heart, heart, smooth muscle, cells of the immune system. If excess or insufficient histamine is produced, and these abnormal amounts stimulate H2R, then such a condition can be treated, diagnosed, etc., in accordance with the present invention.

By the phrase "assessing expression of H2R," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on H2R disorders is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having a H2R disorder, or, susceptible to such a disorder, comprising, e.g., detecting the expression levels of H2R. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose a disorder.

Expression can be assessed in any sample comprising any tissue or cell type, body fluid, etc., as discussed for other methods of the present invention, including cells from the stomach, intestine, heart, and immune cells can be used, or cells derived from a tissue. By the phrase "cells derived from a tissue," it is meant that the derived cells originate from the tissue, e.g., when metastasis from a primary tumor site has occurred, when a progenitor-type or pluripotent cell gives rise to other cells, or when cells are an in vitro culture from primary cells obtained from the tissue.

Identifying Agent Methods

The present invention also relates to methods of identifying agents that modulate the biological activity of H2R, comprising, in any effective order, one or more of the following steps, e.g., contacting a cell population (i.e., containing cells that express H2R) with a test agent under conditions effective for said test agent to modulate the activity of H2R in said cell population, and determining whether said test agent modulates said H2R. An agent can modulate activity of H2R at any level, including at the protein level, as well as at the gene level, e.g., by effecting transcription, translation, and/or perdurance of the nucleic acid or polypeptide (e.g., degradation, stability, etc.) product in the cell.

Contacting the cell population with the test agent can be accomplished by any suitable method and/or means that places the agent in a position to affect the biological activity of the H2R present in cells within the population. The choice of the method and/or means can depend upon the nature of the agent and the condition and type of the cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the cells, it can be determined whether the test agent modulates H2R activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc.

A test agent can be of any molecular composition, e.g., chemical compounds, biomolecules, such as polypeptides, lipids, nucleic acids (e.g., antisense to a polynucleotide sequence selected from SEQ ID NO 1, carbohydrates, antibodies, ribozymes, double-stranded RNA, etc.

Any cell line which expresses H2R can be utilized in such assay methods. For instance, cell lines can be engineered to express H2R. Examples of cells engineered to express the incomplete H2R include, e.g., COS7 and L-cells. See, e.g., Fukushima et al.; U.S. Pat. No. 5,885,824. Cell lines and methods of introducing genes into them have been discussed in a previous section. Typically, a cell line can be transformed with an expressible gene coding for H2R, where the term "expressible" indicates that the coding sequence is operably linked to any expression sequences necessary for it to achieve transcription, translation, and transport to the appropriate compartment (e.g., the cell membrane, if the H2R is to be expressed on the cell surface). Such sequences include, e.g., enhancer sequences, promoter sequences, sequences that mediate ribosome binding of a transcribed RNA to a ribosome, transcription termination sequences, polyadenylation sequences, etc. These sequences can also be referred to as expression control sequences and are discussed in more detail elsewhere.

Cell lines used to identify modulators can be transformed with a polynucleotide construct comprising an expressible human H2R polynucleotide, whereby said H2R expression is achieved. The term "transformed" indicates that an exogenous polynucleotide has been introduced into the cells in such a way that the polynucleotide can be expressed by the cell, e.g., constitutively or inducibly. A "construct" means any recombinant polynucleotide molecule, such as plasmids, viruses, phages, and other vector carriers utilized to introduce polynucleotides into a cell. The phrase "whereby said H2R expression is achieved" indicates that expression of H2R by the cell is mediated by the construct comprising the polynucleotide coding for H2R.

A biological activity of the H2R includes any function of the receptor protein. H2R is part of a signaling pathway that begins with its coupling to transduction proteins, including, but not limited to, G-proteins and kinases, such as GRKs, upon activation by an extracellular ligand. As discussed earlier, stimulation or activation of H2R has many different effects, including, but not limited to, cAMP production, phospholipid methylation, changes in calcium conductance, mobilization of intracellular calcium pools, calcium release, inhibition of phospholipase A, receptor protein phosphorylation, etc. An agent which interferes with any of these effects can be said to "modulate the activity of H2R." For example, suppose histamine is administered to a cell expressing H2R, and measurable cAMP is produced as a result. An antagonist that is administered to the cell which blocks the production of cAMP in the presence of histamine can be described as modulating the biological activity of the receptor. Similarly, agents which block calcium release, phosphorylation (e.g. at residues 364, 366, 367, 369, 370, 374, 378, 393, 397, 402, 416, and/or 419), down-regulation, desensitization, etc., are agents that modulate receptor activity.

The biological activity of the H2R can be determined routinely. For instance, there are many conventional assays for cAMP activity, and they can be performed as described in, e.g., Fukushima et al., *Biochem. J.*, 310:553–558, 1995. Commercial kits are also available, e.g., HEFP (LJL Biosystems/Molecular Devices), HTRF (Cis bio), Enzyme fragment complementation (DiscoveRX), and ELISA (Tropix/Applied Biosystems). Similarly, assays for calcium can be performed routinely, e.g., using commercial kits, e.g., from Molecular Devices Corporation (FLIPR Calcium Assay Kit).

Phosphorylation can be measured when the assay is performed in the presence of a labeled ATP, e.g., a gamma-labeled ATP, such as $^{32}$P-ATP. The resulting labeled phosphorylated H2R is separated from the gamma-labeled ATP. Separation and detection of the phosphoprotein can be achieved through any suitable method, e.g., filters or electrophoresis. When a radioactive label is utilized, the labeled phosphoprotein can be separated from the unreacted gamma-$^{32}$P-ATP using an affinity membrane or gel electrophoresis, and then visualized on the gel using autoradiography.

Non-radioactive methods can also be used. Methods can utilize an antibody which recognizes the phosphorylated H2R, e.g., an anti-phosphoserine or anti-phosphothreonine antibody. For instance, after the assay is performed, a lysate can be prepared from it, subjected to size separation if desired, then phosphorylation of the receptor can be measured by Western blotting using an anti-phosphoserine or anti-phosphothreonine antibody. The antibody can be labeled with a detectable label, e.g., an enzyme, such as HRP, avidin or biotin, chemiluminescent reagents, etc. Other methods can utilize ELISA formats, affinity membrane separation, fluorescence polarization assays, luminescent assays, etc.

Therapeutics

Selective polynucleotides, polypeptides, specific-binding partners thereto, and other compounds, can be utilized in therapeutic applications, especially to treat diseases and conditions associated with H2R and histaminergic diseases. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germline correction, antisense), administration of effective compounds, etc.

Polynucleotides and polypeptides can be used to interfere with function, expression (e.g., antisense as a therapeutic agent), assembly, etc. RNA interference can be used in vitro and in vivo to silence H2R when its expression contributes to a disease (but also for other purposes, e.g., to identify the gene's function to change a developmental pathway of a cell, etc.). See, e.g., Sharp and Zamore, *Science*, 287:2431–2433, 2001; Grishok et al., *Science*, 287:2494, 2001.

The activity of the H2R receptor can be modulated by altering the function of its carboxy-terminal tail, (e.g., 360–422 of SEQ ID NO 2). Modulation can be agonism or antagonism, depending upon which effect would alleviate the condition. For instance, antagonism of the H2R is useful in the treatment of parietal cell disorders, such as peptic ulcer and dyspepsia. Peptides and other compounds can be used to block H2R coupling molecules (such as GRKs) from binding to the H2R receptor, or from interacting functionally with the receptor. For instance, the H2R carboxy-terminal tail contains phosphorylation sites for GRK and other kinases. By blocking phosphorylation at these residues, the activity of the H2R receptor can be modulated. Blockade can be accomplished using, e.g., peptides which mimic the carboxy-tail (e.g., 360–422 of SEQ ID NO 2, and fragments thereof), or compounds which prevent kinase phosphorylation.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intraarterial, and intrathecal, etc. They can be administered alone, or in combination with any ingredient(s), active or inactive.

In addition to therapeutics, per se, the present invention also relates to methods of treating a disease associated with H2R or histaminergic dysfunction, comprising, e.g., administering to a subject in need thereof a therapeutic agent which is effective for regulating expression of said H2R and/or which is effective in treating said disease. The term "treating" is used conventionally, e.g., the management or care of a subject for the purpose of combating, alleviating, reducing, relieving, improving the condition of, etc., of a disease or disorder. Diseases or disorders which can be treated in accordance with the present invention include, but are not limited to, peptic disorders, gastric and duodenal ulcers, dyspepsia, gastro-esophageal reflux disease, parietal and stomach cell disorders, and other disorders associated with aberrant histaminergic function (e.g., excess histamine, or insufficient histamine).

Any agent which "treats" the disease can be used. Such an agent can be one which regulates the activity or expression of the H2R. As discussed above, agents can modulate the activity of the H2R, e.g., by altering the function of the carboxy-terminal tail. Regulation or modulation can be by antagonist or an agonist. For instance, if the condition was a result of an excess of histamine (e.g., a peptic ulcer), administration of a compound which blocks the receptor function (e.g., by blocking a GRK) would be said to treat the disease and regulate the H2R. Many other possible situations are possible.

Antisense

Antisense polynucleotide (e.g., RNA) can also be prepared from a polynucleotide according to the present invention, preferably an anti-sense to a sequence of SEQ ID NOS 1, such as positions 1182–1368 of SEQ ID NO 1). Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, nonnaturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Transgenic Animals

The present invention also relates to transgenic animals comprising H2R genes. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., *Exp. Physiol.*, 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The H2R nucleic acid present in the construct or transgene can be naturally-occurring wild-type, polymorphic, or mutated.

Along these lines, polynucleotides of the present invention can be used to create transgenic animals, e.g. a non-human animal, comprising at least one cell whose genome comprises a functional disruption of H2R. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the H2R gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its H2R genes has been "knocked-out." Knock-outs can be homozygous or heterozygous.

For creating functional disrupted genes, and other gene mutations, homologous recombination technology is of special interest since it allows specific regions of the genome to be targeted, e.g., the carboxy-terminal tail of the H2R. Using homologous recombination methods, genes can be specifically-inactivated, specific mutations can be introduced, and exogenous sequences can be introduced at specific sites. These methods are well known in the art, e.g., as described in the patents above. See, also, Robertson, *Biol. Reproduc.*, 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, the H2R locus can be disrupted in mouse ES cells using a positive-negative selection method (e.g., Mansour et al., *Nature*, 336:348–352, 1988). In this method, a targeting vector can be constructed which comprises a part of the gene to be targeted. A selectable marker, such as neomycin resistance genes, can be inserted into a H2R exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional H2R genes can be useful in a variety of applications, including, as an animal model for diseases associated with aberrant histaminergic function diseases, for drug screening assays for agents that regulate H2R function), as a source of tissues deficient in H2R activity, and any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824.

A recombinant H2R nucleic acid refers to a gene which has been introduced into a target host cell and optionally modified, such as cells derived from animals, plants, bacteria, yeast, etc. A recombinant H2R includes completely synthetic nucleic acid sequences, semi-synthetic nucleic acid sequences, sequences derived from natural sources, and chimeras thereof "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant H2R has been stably integrated into the genome of the animal. The H2R nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a fictionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue- and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985-2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratory,* Cold Spring Harbor, N.Y., 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a H2R gene, H2R polypeptide, or antibody specific for H2R in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found. Reference materials For other aspects of the polynucleotides, reference is made to standard textbooks of molecular biology. See, e.g., Hames et al., *Polynucleotide Hybridization,* IL Press, 1985; Davis et al., *Basic Methods in Molecular Biology,* Elsevir Sciences Publishing, Inc., New York, 1986; Sambrook et al., *Molecular Cloning,* CSH Press, 1989; Howe, *Gene Cloning and Manipulation,* Cambridge University Press, 1995; Ausubel et al., *Current Protocols in Molecular Biology,* John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

What is claimed is:

1. An isolated human H2R polynucleotide which codes without interruption for an amino acid sequence set forth in SEQ ID NO 2, or a complete complement thereto.

2. An isolated human H2R polynucleotide comprising,
a polynucleotide sequence having 95% or more sequence identity along the entire length of the polynucleotide sequence from nucleotide positions 103–1368 as set forth in SEQ ID NO 1 and which codes without interruption for H2R, or a complete complement thereto, wherein said polynucleotide hybridizes under high stringency conditions comprising 5×SSC, 0.5% SDS, 100 µg/ml denatured salmon sperm DNA and 50% formamide, at 42° C. to the complete complement of the sequence set forth in SEQ ID NO:1, and wherein said polynucleotide codes for a polypeptide that, upon activation by histamine, leads to the accumulation of cAMP.

3. An isolated H2R polynucleotide, comprising:
a polynucleotide coding for amino acids 360–422 of SEQ ID NO 2, or a polynucleotide fragment thereof comprising at least 25 nucleotides, or complete complements thereto, wherein said fragment can be used as a polymerase chain reaction primer.

4. An isolated H2R polynucleotide of claim 3, consisting of: a polynucleotide coding for amino acids 360–422 of SEQ ID NO 2, or a complete complement thereto.

5. An isolated transformed mammalian cell comprising:
a polynucleotide construct comprising a human H2R polynucleotide of claim 2 operatively linked to an expression control sequence.

6. An isolated transformed cell of claim 5, wherein said human H2R polynucleotide has the polynucleotide sequence from nucleotides 103–1368 as set forth in SEQ ID 1.

7. An isolated transformed cell of claim 5, wherein said human H2R polynucleotide has the amino acid sequence set forth in SEQ ID 2.

8. An isolated transformed cell of claim 5, wherein said expressible human H2R polynucleotide is integrated into the chromosome of said cell.

9. An isolated human H2R polynucleotide of claim 1, comprising the polynucleotide sequence from nucleotide positions 103–1368 as set forth in SEQ ID NO:1, or a complete complement thereto.

10. An isolated H2R polynucleotide of claim 1, wherein said polynucleotide comprises the polynucleotide sequence from nucleotide positions 1180–1368 as set forth in SEQ ID NO:1.

11. A method of producing a human H2R polynucleotide, comprising:
comprising expressing a polynucleotide of claim 1 operatively linked to an expression control sequence under conditions effective to achieve production of said H2R coded for by said polynucleotide.

12. A method of producing a human H2R polynucleotide, comprising:
comprising expressing a polynucleotide of claim 2 operatively linked to an expression control sequence under conditions effective to achieve production of said H2R coded for by said polynucleotide.

13. A method of producing a human H2R polynucleotide, comprising:
comprising expressing a polynucleotide of claim 9 operatively linked to an expression control sequence under conditions effective to achieve production of said H2R coded for by said polynucleotide.

14. A method of producing a human H2R polynucleotide, comprising:
comprising expressing a polynucleotide of claim 10 operatively linked to an expression control sequence under conditions effective to achieve production of said H2R coded for by said polynucleotide.

* * * * *